(12) United States Patent
Suganuma et al.

(10) Patent No.: US 10,117,965 B1
(45) Date of Patent: Nov. 6, 2018

(54) INTRAOCULAR LENS MATERIAL

(71) Applicant: MENICON CO., LTD, Nagoya-shi, Aichi (JP)

(72) Inventors: Yuya Suganuma, Owariasahi (JP); Hiroko Nomura, Nagoya (JP); Tatsuya Ojio, Kasugai (JP)

(73) Assignee: MENICON CO., LTD., Nagoya-shi (JP)

( * ) Notice: Subject to any disclaimer, the term of this patent is extended or adjusted under 35 U.S.C. 154(b) by 0 days.

(21) Appl. No.: 15/772,273

(22) PCT Filed: Jul. 27, 2017

(86) PCT No.: PCT/JP2017/027176
§ 371 (c)(1),
(2) Date: Apr. 30, 2018

(87) PCT Pub. No.: WO2018/021455
PCT Pub. Date: Feb. 1, 2018

(30) Foreign Application Priority Data

Jul. 28, 2016 (JP) ................. 2016-148426

(51) Int. Cl.
*A61L 27/16* (2006.01)
*A61L 27/50* (2006.01)
*C08F 222/14* (2006.01)
*C08F 220/30* (2006.01)
*C08F 220/28* (2006.01)

(52) U.S. Cl.
CPC ............ *A61L 27/16* (2013.01); *A61L 27/50* (2013.01); *C08F 220/30* (2013.01); *C08F 222/14* (2013.01); *A61L 2430/16* (2013.01); *C08F 2220/286* (2013.01); *C08F 2220/301* (2013.01)

(58) Field of Classification Search
CPC ...... A61L 27/16; A61L 27/50; A61L 2430/16; C08F 222/14; C08F 220/30; C08F 2220/301; C08F 2220/286
USPC ......................................................... 526/320
See application file for complete search history.

(56) References Cited

U.S. PATENT DOCUMENTS

| | | | |
|---|---|---|---|
| 6,140,438 A | 10/2000 | Ojio et al. | |
| 7,387,642 B2* | 6/2008 | Benz | A61F 2/16 524/556 |
| 9,310,624 B2* | 4/2016 | Argal | A61L 27/26 |
| 2006/0276606 A1* | 12/2006 | Benz | A61F 2/16 526/320 |
| 2009/0082553 A1 | 3/2009 | Satake et al. | |
| 2013/0107201 A1* | 5/2013 | Argal | A61L 27/26 351/159.44 |
| 2017/0121439 A1 | 5/2017 | Emori et al. | |
| 2017/0181847 A1* | 6/2017 | Argal | A61L 27/26 |

FOREIGN PATENT DOCUMENTS

| | | |
|---|---|---|
| JP | H11-56998 A | 3/1999 |
| JP | 2006-291006 A | 10/2006 |
| JP | 2015-502763 A | 1/2015 |
| WO | 2006/113290 A1 | 10/2006 |
| WO | 2012/004746 A2 | 1/2012 |
| WO | 2013/040434 A1 | 3/2013 |
| WO | 2015/070981 A1 | 5/2015 |
| WO | 2016/002936 A1 | 1/2016 |

OTHER PUBLICATIONS

Oct. 3, 2017 International Search Report issued in International Patent Application No. PCT/JP2017/027176.
Oct. 3, 2017 Written Opinion issued in International Patent Application No. PCT/JP2017/027176.

* cited by examiner

*Primary Examiner* — Michael Bernshteyn
(74) *Attorney, Agent, or Firm* — Oliff PLC

(57) ABSTRACT

An intraocular lens material disclosed in the present description includes an aromatic ring-containing acrylate structural unit, an alkoxyalkyl methacrylate structural unit including an alkoxy group having 4 or less carbon atoms, a hydrophilic structural unit based on a hydrophilic monomer, and a cross-linking structural unit based on a cross-linkable monomer.

10 Claims, 2 Drawing Sheets

INTRAOCULAR LENS MATERIAL

TECHNICAL FIELD

The present invention relates to an intraocular lens material.

BACKGROUND ART

Progress in small-incision cataract surgery has led to the development of soft, flexible and foldable materials suitable for intraocular lenses. In particular, acrylic materials are desirable because they have a high refractive index and unfold slowly after insertion into an eye. However, when a material with enhanced shape recoverability is used for a lens, the elongation percentage of the lens becomes low. This material is brittle and easily torn when the lens has, for example, a flaw. To insert a lens into an eye through a minimum incision, it is preferable to use a material with a large elongation percentage so that the lens is prevented from cracking and tearing.

One previously proposed intraocular lens material is a polymer obtained by polymerizing polymerizable components including a hydrophilic monomer such as a hydroxyl group-containing alkyl (meth)acrylate, a (meth)acrylamide monomer, or an N-vinyl lactam, and the water absorption percentage of the intraocular lens material is 1.5 to 4.5% by mass (see, for example, PTL 1). This intraocular lens material is excellent in flexibility and has a high refractive index. Therefore, a lens with a reduced thickness can be provided, and the lens in a folded state can be inserted through an incision. Moreover, the intraocular lens material has excellent transparency and can reduce the occurrence of glistening.

CITATION LIST

Patent Literature

PTL 1: Japanese Unexamined Patent Application Publication No. 11-56998

SUMMARY OF THE INVENTION

Technical Problem

In an acrylic elastomer using the intraocular lens material in PTL 1, ester moieties may undergo hydrolysis, and dissolution of a hydrolysate may occur although the amount of dissolution is very small. There is therefore a need for a material that can provide an intraocular lens from which only a reduced amount of a hydrolysate dissolves.

The present invention has been made in view of the foregoing circumstances, and it is a primary object to provide an intraocular lens material from which only a reduced amount of the hydrolysate dissolves in an aqueous solution.

Solution to Problem

To achieve the above object, the present inventors have conducted extensive studies and found that, when an intraocular lens material containing an acrylate as a base material contains a specific methacrylate, the amount of a hydrolysate dissolved in an aqueous solution can be further reduced while the desired properties of the intraocular lens material are maintained or improved. Thus, the present invention has been completed.

Accordingly, an intraocular lens material disclosed in the present description comprises: an aromatic ring-containing acrylate structural unit; an alkoxyalkyl methacrylate structural unit including an alkoxyalkyl group having 4 or less carbon atoms; a hydrophilic structural unit based on a hydrophilic monomer; and a cross-linking structural unit based on a cross-linkable monomer.

With this intraocular lens material, the amount of a hydrolysate dissolved from the intraocular lens material in an aqueous solution can be further reduced. The reason that this effect is obtained may be, for example, as follows. For example, methacrylate is a material harder than acrylate because of the presence of a methyl group but may resist attack by water. Therefore, hydrolysis resistance may be improved. In the case that the alkoxyalkyl group having 4 or less carbon atoms is included, the number of carbon atoms is preferable, and therefore the intraocular lens material may not be excessively hard and may have sufficient flexibility. Moreover, the intraocular lens material containing the alkoxyalkyl group having 4 or less carbon atoms may be preferred in terms of flexibility, reduction in stickiness, and the ability to reduce the occurrence of glistening. The alkoxyalkyl group may be represented by, for example, chemical formula (1).

$$C_nH_{2n+1}OC_mH_{2m}- \quad ((n+m)\leq 4) \quad \text{chemical formula (1)}$$

DESCRIPTION OF EMBODIMENTS

Figure 1:
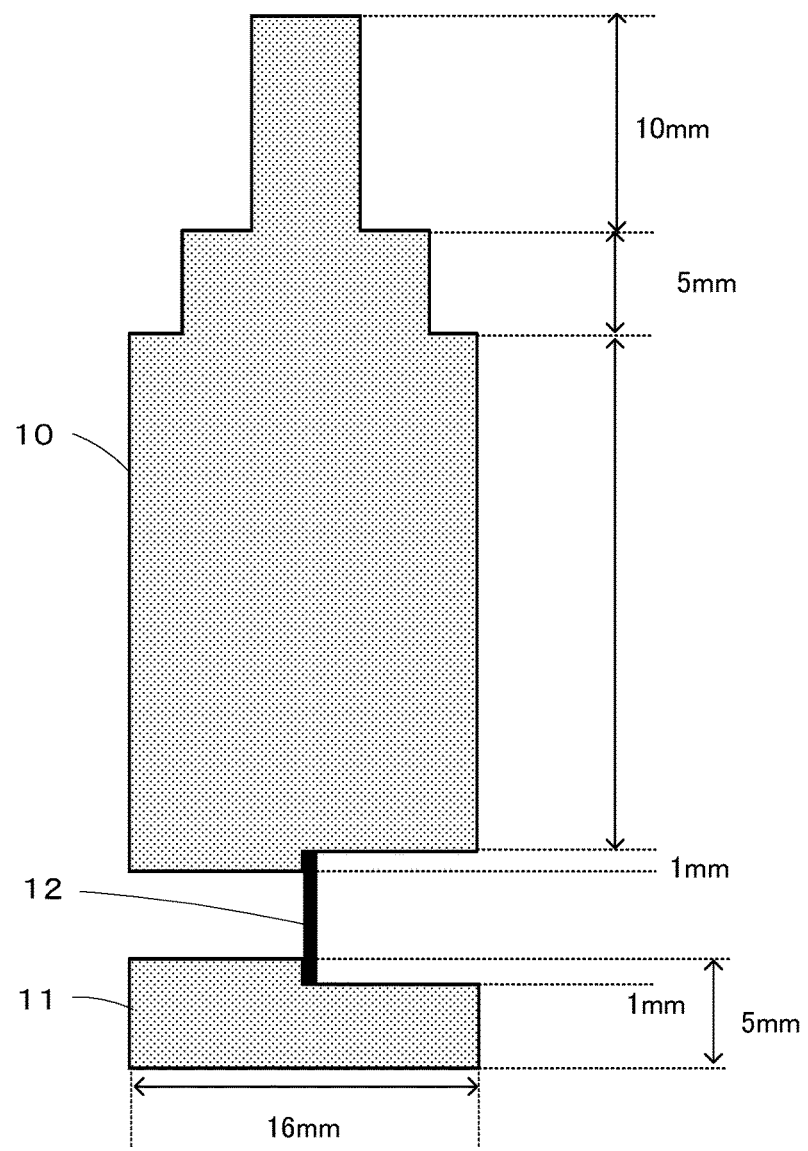
FIG. 1 is a side view of an indenter 10 and a jig 11 that are used for compressive load measurement.

An intraocular lens material disclosed in an embodiment comprises: an aromatic ring-containing acrylate structural unit; an alkoxyalkyl methacrylate structural unit including an alkoxyalkyl group having 4 or less carbon atoms; a hydrophilic structural unit based on a hydrophilic monomer; and a cross-linking structural unit based on a cross-linkable monomer. This intraocular lens material contains, as a base material, the aromatic ring-containing acrylate structural unit and the alkoxyalkyl methacrylate structural unit including the alkoxyalkyl group having 4 or less carbon atoms. The intraocular lens material may further contain, as a base material, an alkyl acrylate structural unit including an alkyl group having 1 to 20 carbon atoms. The base material is component forming the main structure of the intraocular lens material. As shown in chemical formula (2), the intraocular lens material may contain, as a base material, aromatic ring-containing acrylate structural units A, alkoxyalkyl methacrylate structural units B, and alkyl acrylate structural units C. In chemical formula (2), a, b, and c are any integers. The aromatic ring-containing acrylate structural units A, the alkoxyalkyl methacrylate structural units B, and the alkyl acrylate structural units C are bonded to a carbon chain in an arbitrary manner, and adjacent structural units may be the same or different. A functional group $R^1$ is an aromatic ring-containing functional group, and a functional group $R^2$ is an alkoxyalkyl group including an alkoxy group and having 4 or less carbon atoms. A functional group $R^3$ is an alkyl group having 1 to 20 carbon atoms. As used herein, acrylate having an acryloyl group and methacrylate having a methacryloyl group are collectively referred to as "(meth) acrylate." For the sake of convenience of description, a structural unit included in a polymer is designated by the name of a corresponding monomer. Monomers exemplified in the description of a polymer structure have structures in which their polymerizable groups are bonded to other structural units. For example, a monomer exemplified as "(meth) acrylate" in the description of a polymer structure is present as a "(meth)acrylate structural unit" in the polymer. In this structural unit, another structural unit is bonded (polymerized) to a double bond of the (meth)acrylate.

[Chem. 1]

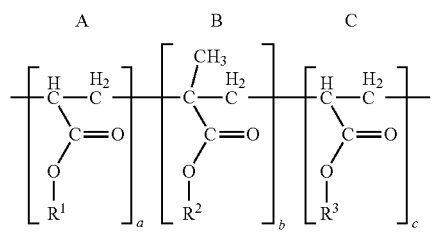

Chemical formula (2)

In this intraocular lens material, the aromatic ring-containing acrylate structural unit is a structural unit based on an aromatic ring-containing acrylate used as a base material monomer. This aromatic ring-containing acrylate may be a component having the function of increasing the refractive index of the intraocular lens material. This aromatic ring-containing acrylate structural unit may have a phenoxy group, an alkylene group having 2 or less carbon atoms, and an acrylate bond moiety. Examples of the aromatic ring-containing acrylate include phenoxyethyl acrylate, phenylethyl acrylate, benzyl acrylate, phenyl acrylate, and pentabromophenyl acrylate. These may be used alone, or a mixture of two or more may be used. Of these, at least one of phenoxyethyl acrylate, phenylethyl acrylate, and benzyl acrylate is preferred because their effect of increasing the refractive index is high. Phenoxyethyl acrylate is particularly preferred because it can further enhance flexibility. Preferably, the amount of the aromatic ring-containing acrylate is within the range of from 15 parts by mass to 80 parts by mass inclusive based on 100 parts by mass of the total amount of the base material. More preferably, the amount of the aromatic ring-containing acrylate is from 30 parts by mass to 80 parts by mass inclusive based on 100 parts of the base material because it is desirable that the intraocular lens material has a high refractive index even in a moistened state.

In the intraocular lens material, the alkoxyalkyl methacrylate structural unit including the alkoxyalkyl group having 4 or less carbon atoms is a structural unit based on an alkoxyalkyl methacrylate used as a base material monomer. The alkoxyalkyl group in the alkoxyalkyl methacrylate may be, for example, a group represented by chemical formula (1) above. Examples of the alkoxy group include a methoxy group and an ethoxy group. Examples of the alkylene group to which the alkoxy group is bonded include a methylene group and an ethylene group. The alkoxyalkyl methacrylate is preferably at least one of methoxyethyl methacrylate and ethoxyethyl methacrylate and more preferably ethoxyethyl methacrylate. The amount of the alkoxyalkyl methacrylate is preferably within the range of from 10 parts by mass to 70 parts by mass inclusive based on 100 parts by mass of the total amount of the base material. From the viewpoint that the degree of hydrolysis can be further reduced and from the viewpoint of ease of folding, the amount of the alkoxyalkyl methacrylate is more preferably from 20 parts by mass to 40 parts by mass inclusive based on 100 parts by mass of the base material. An example of the structure of the intraocular lens material is shown in chemical formula (3). In this example, the base material is 2-phenoxyethyl acrylate (POEA), ethyl acrylate (EA), and ethoxyethyl methacrylate (ETMA). In chemical formula (3), a, b, and c are any integers. The aromatic ring-containing acrylate structural units A, the alkoxyalkyl methacrylate structural units B, and the alkyl acrylate structural units C are bonded to a carbon chain in an arbitrary manner, and adjacent structural units may be the same or different.

[Chem. 2]

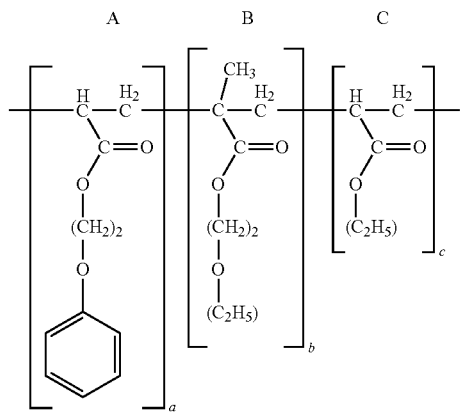

Chemical formula (3)

In the intraocular lens material, the alkyl acrylate structural unit including the alkyl group having 1 to 20 carbon atoms is a structural unit based on an alkyl acrylate used as a base material monomer. The alkyl acrylate including the alkyl group having 1 to 20 carbon atoms may be a component having the function of improving the shape recoverability and flexibility of the intraocular lens material. Examples of the alkyl acrylate include straight-chain, branched-chain, and cyclic alkyl acrylates such as methyl acrylate, ethyl acrylate, propyl acrylate, butyl acrylate, pentyl acrylate, hexyl acrylate, heptyl acrylate, nonyl acrylate, stearyl acrylate, octyl acrylate, decyl acrylate, lauryl acrylate, pentadecyl acrylate, 2-ethylhexyl acrylate, cyclopentyl acrylate, and cyclohexyl acrylate. Other examples of the alkyl acrylate include fluorine-containing alkyl (meth)acrylates such as 2,2,2-trifluoroethyl acrylate, 2,2,3,3-tetrafluoropropyl acrylate, 2,2,3,3-tetrafluoro-t-pentyl acrylate, 2,2,3,4,4,4-hexafluorobutyl acrylate, 2,2,3,4,4,4-hexafluoro-t-hexyl acrylate, 2,3,4,5,5,5-hexafluoro-2,4-bis (trifluoromethyl)pentyl acrylate, 2,2,3,3,4,4-hexafluorobutyl acrylate, 2,2,2,2',2',2'-hexafluoroisopropyl acrylate, 2,2,3,3, 4,4,4-heptafluorobutyl acrylate, and 2,2,3,3,4,4,5,5-octafluoropentyl acrylate. These may be used alone, or a mixture of two or more may be used. Of these, alkyl acrylates including an alkyl group having 1 to 5 carbon atoms are preferred because their effect of improving the shape recoverability and flexibility is high, and ethyl acrylate and butyl acrylate are particularly preferably used. Preferably, the amount of the alkyl acrylate is within the range of from 0 parts by mass to 35 parts by mass inclusive based on 100 parts by mass of the total amount of the base material. The alkyl acrylate is regarded as one of the base material but is not necessarily an essential component. In terms of the flexibility and shape recoverability, the amount of the alkyl acrylate may be appropriately adjusted at the above ratio.

In the intraocular lens material, the hydrophilic structural unit is a structural unit based on a hydrophilic monomer. The hydrophilic monomer is a component that provides hydrophilicity to the intraocular lens material and may be a component having the function of facilitating a reduction in the occurrence of glistening in the intraocular lens material. The hydrophilic monomer may include, for example, at least one of hydroxyl group-containing alkyl (meth)acrylates including an alkyl group having 1 to 20 carbon atoms, (meth)acrylamide monomers, and N-vinyl lactams. An additional hydrophilic monomer other than the above hydrophilic monomers may be included. Examples of the hydroxyl group-containing alkyl (meth)acrylate include: hydroxyalkyl (meth)acrylates such as hydroxyethyl (meth)acrylate, hydroxypropyl (meth)acrylate, hydroxybutyl (meth)acrylate, and hydroxypentyl (meth)acrylate; and dihydroxyalkyl (meth)acrylates such as dihydroxypropyl (meth)acrylate, dihydroxybutyl (meth)acrylate, and dihydroxypentyl (meth)acrylate. Examples of the (meth)acrylamide monomer include N,N-dialkyl(meth)acrylamides such as N,N-dimethyl(meth)acrylamide, N,N-diethyl(meth)acrylamide, and N,N-dipropyl(meth)acrylamide; and N,N-dialkylaminoalkyl(meth)acrylamides such as N,N-dimethylaminopropyl(meth)acrylamide and N,N-diethylaminopropyl (meth)acrylamide. Examples of the N-vinyl lactam include N-vinylpyrrolidone, N-vinylpiperidone, and N-vinylcaprolactam. Examples of the additional hydrophilic monomer include diethylene glycol mono(meth)acrylate, triethylene glycol mono(meth)acrylate, propylene glycol mono(meth) acrylate, (meth)acrylic acid, 1-methyl-3-methylene-2-pyrrolidinone, maleic anhydride, maleic acid, maleic acid derivatives, fumaric acid, fumaric acid derivatives, aminostyrene, and hydroxystyrene. The above-described hydrophilic monomers may be used alone, or a mixture of two or more may be used. Among these hydrophilic monomers, hydroxyl group-containing alkyl (meth)acrylates and (meth)acrylamide monomers are preferred because their function of facilitating a reduction in the occurrence of glistening is high, and 2-hydroxyethyl methacrylate is particularly preferred. Preferably, the content of the hydrophilic monomer is within the range of from 15 parts by mass to 35 parts by mass inclusive by the outside ratio based on 100 parts by mass of the total amount of the base material. When the content of the hydrophilic monomer is within this range, the effect of facilitating a reduction in the occurrence of glistening can be sufficiently obtained, and no significant burden and difficulty arise when the intraocular lens material in a dry state is folded.

In the intraocular lens material, the cross-linking structural unit is a structural unit based on a cross-linkable monomer. The cross-linkable monomer may be a component that has the function of controlling the flexibility of the intraocular lens material, the function of imparting good mechanical properties, the function of further improving the shape recoverability, and the function of improving copolymerizability of the polymerizable components such as the hydrophilic monomer and other polymerizable monomers. Examples of the cross-linkable monomer include butanediol di(meth)acrylate, ethylene glycol di(meth)acrylate, diethylene glycol di(meth)acrylate, triethylene glycol di(meth) acrylate, propylene glycol di(meth)acrylate, dipropylene glycol di(meth)acrylate, diallyl fumarate, allyl (meth)acrylate, vinyl (meth)acrylate, trimethylolpropane tri(meth)acrylate, methacryloyloxyethyl (meth)acrylate, divinylbenzene, diallyl phthalate, diallyl adipate, triallyl diisocyanate, α-methylene-N-vinylpyrrolidone, 4-vinylbenzyl (meth) acrylate, 3-vinylbenzyl (meth)acrylate, 2,2-bis((meth)acryloyloxyphenyl)hexafluoropropane, 2,2-bis((meth)acryloyloxyphenyl)propane, 1,4-bis(2-(meth) acryloyloxyhexafluoroisopropyl)benzene, 1,3-bis(2-(meth) acryloyloxyhexafluoroisopropyl)benzene, 1,2-bis(2-(meth) acryloyloxyhexafluoroisopropyl)benzene, 1,4-bis(2-(meth) acryloyloxyisopropyl)benzene, 1,3-bis(2-(meth) acryloyloxyisopropyl)benzene, and 1,2-bis(2-(meth) acryloyloxyisopropyl)benzene. These may be used alone, or a mixture of two or more may be used. Among these cross-linkable monomers, at least one of butanediol di(meth) acrylate and ethylene glycol di(meth)acrylate is particularly preferred because the effect of controlling the flexibility, the effect of imparting good mechanical properties, and the effect of improving the shape recoverability and copolymerizability are high. Preferably, the content of the cross-linkable monomer is within the range of from 2 parts by mass to 4 parts by mass inclusive by the outside ratio based on 100 parts by mass of the total amount of the base material. The content is preferably 2 parts by mass or more from the viewpoint of imparting the shape recoverability and reducing the occurrence of glistening. The content is preferably 4 parts by mass or less because the intraocular lens material can have an elongation percentage high enough to allow insertion from a small incision.

The intraocular lens material may contain other additional components such as an ultraviolet absorber and a coloring agent. Examples of the ultraviolet absorber include: benzophenones such as 2-hydroxy-4-methoxybenzophenone and 2-hydroxy-4-octoxybenzophenone; benzotriazoles such as 2-(2'-hydroxy-5'-methacryloxyethyleneoxy-t-butylphenyl)-5-methyl-benzotriazole, 2-(2'-hydroxy-5'-methylphenyl) benzotriazole, and 5-chloro-2(3'-t-butyl-2'-hydroxy-5'-methylphenyl)benzotriazole; salicylic acid derivatives; and hydroxyacetophenone derivatives. Preferably, the amount of the ultraviolet absorber added is, for example, within the range of from 0.05 parts by mass to 3 parts by mass inclusive by the outside ratio based on 100 parts by mass of the total amount of the base material. For example, to correct cyanopsia, it is preferable to use a yellow or orange coloring agent. Examples of the coloring agent include: a dye described in Japanese Unexamined Patent Application Publication No. 2006-291006; oil-soluble dyes such as CI Solvent Yellow and CI Solvent Orange listed in the Color Index International (CI); disperse dyes such as CI Disperse Yellow and CI Disperse Orange listed in the Color Index International (CI); and vat dyes. Preferably, the amount of the coloring agent added is within the range of from 0.01 parts by mass to 3 parts by mass inclusive by the outside ratio based on 100 parts by mass of the total amount of the base material.

For example, a radical polymerization initiator or a photopolymerization initiator may be added for polymerization to obtain the intraocular lens material. For example, a polymerization method in which a radical polymerization initiator is added followed by heating or irradiation with electromagnetic waves such as microwaves, ultraviolet radiation, or radiation (γ radiation) may be used. Examples of the radical polymerization initiator include azobisisobutyronitrile, azobisdimethylvaleronitrile, benzoyl peroxide, t-butyl hydroperoxide, and cumene hydroperoxide. When a light beam, for example, is used for polymerization, it is preferable to further add a photopolymerization initiator or a sensitizer. Examples of the photopolymerization initiator include: benzoin-based compounds such as methyl orthobenzoyl benzoate; phenone-based compounds such as 2-hydroxy-2-methyl-1-phenylpropane-1-one; thioxanthone-based compounds such as 1-hydroxycyclohexyl phenyl ketone, 1-phenyl-1,2-propanedione-2-(o-ethoxycarbonyl) oxime, and 2-chlorothioxanthone; dibenzosuberone; 2-ethylanthraquinone; benzophenone acrylate; benzophenone; and benzil. To allow the polymerization reaction to proceed at a sufficient rate, the amount of the polymerization initiator or sensitizer used is preferably within the range of from 0.01 parts by mass to 2 parts by mass inclusive by the outside ratio based on 100 parts by mass of the total amount of the base material. The intraocular lens material of the present invention may be formed into an intraocular lens using, for example, lathing or molding.

In the intraocular lens material, glistening is less likely to occur. When the material in the form of a lens is evaluated using an experimental method described in the present description, the number of glistening spots per a lens is preferably 15 or less. When the material in the form of a plate is evaluated using the above method, the number of glistening spots per a plate is preferably 6 or less and more preferably 2 or less.

The intraocular lens material has an elongation percentage high enough to allow insertion from a small incision. Specifically, when the material is evaluated using an experimental method described in the present description, the elongation percentage is preferably 170% or more. In terms of the shape recoverability of the intraocular lens material, the elongation percentage is preferably 600% or less.

In the intraocular lens material, the dissolution rate of phenoxyethyl alcohol (POEtOH), which is a hydrolysate of the material, after the material has been stored in water at 100° C. for 30 days is preferably 0.13% by mass or less and more preferably 0.10% by mass or less. In the intraocular lens material, the dissolution rate of POEtOH from the material after the material has been stored in water at 100° C. for 60 days is preferably 0.80% by mass or less and more preferably 0.70% by mass or less. In the intraocular lens material, the dissolution rate of POEtOH from the material after the material has been stored in water at 100° C. for 90 days is preferably 3.30% by mass or less and more preferably 2.80% by mass or less. The smaller the dissolution rate, the more preferred.

In the intraocular lens material, the water absorption percentage (% by mass) of the material is preferably within the range of from 1.5% by mass to 4.5% by mass inclusive. When the water absorption percentage is 1.5% by mass or more, the occurrence of glistening can be reduced. When the water absorption percentage is 4.5% by mass or less, a reduction in flexibility and a reduction in shape recoverability can be suppressed. As described above, the intraocular lens material of the present invention is excellent in flexibility and has a high refractive index. Therefore, a lens with a reduced thickness can be provided, and the lens in a folded state can be inserted through a small incision. Moreover, the intraocular lens material has excellent transparency and can reduce the occurrence of glistening.

With the intraocular lens material in the present embodiment described above in detail, the amount of the hydrolysate dissolved from the intraocular lens material in an aqueous solution can be reduced. The reason that the above effect is obtained is that, for example, the alkoxyalkyl methacrylate including the alkoxyalkyl group having 4 or less carbon atoms is included in addition to the acrylates used as a base material. Generally, methacrylate is a material harder than acrylate because of the presence of a methyl group but resists attack by water, and therefore hydrolysis resistance may be improved. When the number of methacrylate structural units is increased, glistening often occurs easily. Although this mechanism is not clear, since the polymerization rate of acrylic differs from the polymerization rate of methacrylic, phase separation easily occurs, so that glistening seems to occur easily. However, in the intraocular lens material in the present embodiment, the alkoxyalkyl methacrylate is used as methacrylate, so that the ability to reduce the occurrence of glistening does not seem to be lost. Moreover, the alkoxyalkyl methacrylate having 4 or less carbon atoms is preferred in terms of flexibility, reduction in stickiness, and the ability to reduce the occurrence of glistening.

The present invention is not limited to the above-described embodiment. It will be appreciated that the invention can be embodied in various forms so long as they fall within the technical scope of the invention.

EXAMPLES

Examples in which the intraocular lens of the present invention was actually produced will be described as Experimental Examples. Experimental Examples 7 to 14, 18, 20, 21, 23, 24, 26 to 29, 31, 32, 34, 35, 37 to 43, 45 to 53, 55, 57, 59, and 60 correspond to Examples of the present invention. Experimental Examples 1 to 6, 15 to 17, 19, 22, 25, 30, 33, 36, 44, 54, 56, and 58 correspond to Comparative Examples. The present invention is not limited to the following Examples, and it will be appreciated that the invention can be embodied in various forms so long as they fall within the technical scope of the invention.

[Components Used]

Abbreviations for the compounds used in the Experimental Examples are shown below.
<Base Material>
POEA: 2-phenoxyethyl acrylate
EA: ethyl acrylate
POEMA: phenoxyethyl methacrylate
EMA: ethyl methacrylate
BMA: butyl methacrylate
EHMA: ethylhexyl methacrylate
LMA: lauryl methacrylate
MTMA: methoxyethyl methacrylate
ETMA: ethoxyethyl methacrylate
<Hydrophilic Monomer>
HEMA: 2-hydroxyethyl methacrylate
<Cross-Linkable Monomer>
BDDA: 1,4-butanediol diacrylate

[Preparation of Plate-Shaped and Lens-Shaped Intraocular Lens Materials]

Polymerizable components shown in Table 1 were mixed with 0.5 parts by mass of 2,2'-azobis(2,4-dimethylvaleronitrile) as a polymerization initiator by the outside ratio based on 100 parts by mass of the total amount of the base material. The mixture was poured into a mold having a desired lens shape. The mold was placed in an oven at 80° C., and the mixture was subjected to heat polymerization molding for 40 minutes. The polymer obtained was removed from the mold and subjected to elution treatment. Then the resulting polymer was dried in an oven at 60° C., and a lens-shaped intraocular lens material (one of Experimental Examples 1 to 14) was thereby obtained. Similarly, polymerizable components shown in Tables 2 to 4 were used and poured into a mold having a desired plate shape, and the same procedure as described above was repeated to obtain a plate-shaped intraocular lens material (one of Experimental Examples 15 to 60). Plate specimens with the same number (composition) but two different thicknesses were prepared according to the required measurement items. A plate with a thickness of 0.5 mm or 0.8 mm described later is a plate prepared using a mold with a 0.5 mm or 0.8 mm-thick spacer. Each dried plate was punched into a measurement plate with a diameter of 6 mm or 8 mm according to a test purpose.

TABLE 1

| Specimen (Lens) | Base material | | | | | | Hydrophilic monomer | Cross-linkable monomer |
|---|---|---|---|---|---|---|---|---|
| | POEA Parts by mass | EA Parts by mass | POEMA Parts by mass | EHMA Parts by mass | LMA Parts by mass | ETMA Parts by mass | HEMA Parts by mass | BDDA Parts by mass |
| Experimental example 1 | 40 | 20 | | | 40 | | 15 | 4 |
| Experimental example 2 | 60 | | | | 40 | | 15 | 4 |
| Experimental example 3 | 60 | 20 | | | 20 | | 15 | 4 |
| Experimental example 4 | 60 | 20 | | 20 | | | 15 | 4 |
| Experimental example 5 | 30 | 40 | 30 | | | | 15 | 4 |
| Experimental example 6 | | 70 | 30 | | | | 15 | 3 |
| Experimental example 7 | 60 | | | | | 40 | 15 | 2 |
| Experimental example 8 | 60 | 20 | | | | 20 | 15 | 2 |
| Experimental example 9 | 60 | 20 | | | | 20 | 15 | 2.5 |
| Experimental example 10 | 60 | 20 | | | | 20 | 15 | 3 |
| Experimental example 11 | 60 | 15 | | | | 25 | 15 | 2.5 |
| Experimental example 12 | 60 | 15 | | | | 25 | 15 | 3 |
| Experimental example 13 | 60 | 10 | | | | 30 | 15 | 2.5 |
| Experimental example 14 | 60 | 10 | | | | 30 | 15 | 3 |

TABLE 2

| Specimen (Plate) | Base material | | | | | | | Hydrophilic monomer | Cross-linkable monomer |
|---|---|---|---|---|---|---|---|---|---|
| | POEA Parts by mass | EA Parts by mass | EMA Parts by mass | BMA Parts by mass | LMA Parts by mass | MTMA Parts by mass | ETMA Parts by mass | HEMA Parts by mass | BDDA Parts by mass |
| Experimental example 15 | 60 | | 40 | | | | | 15 | 4 |
| Experimental example 16 | 60 | | | 40 | | | | 15 | 4 |
| Experimental example 17 | 60 | 20 | | | 20 | | | 15 | 4 |
| Experimental example 18 | 60 | | | | | 40 | | 15 | 4 |
| Experimental example 19 | 60 | 40 | | | | | | 15 | 4 |
| Experimental example 20 | 60 | 20 | | | | | 20 | 15 | 4 |
| Experimental example 21 | 60 | | | | | | 40 | 15 | 4 |

TABLE 3

| Specimen (Plate) | Base material | | | Hydrophilic monomer | Cross-linkable monomer |
| --- | --- | --- | --- | --- | --- |
| | POEA Parts by mass | EA Parts by mass | ETMA Parts by mass | HEMA Parts by mass | BDDA Parts by mass |
| Experimental example 22 | 60 | 40 | | 15 | 3 |
| Experimental example 23 | 60 | 20 | 20 | 15 | 3 |
| Experimental example 24 | 60 | | 40 | 15 | 3 |
| Experimental example 25 | 60 | 40 | | 15 | 2 |
| Experimental example 26 | 60 | 30 | 10 | 15 | 2 |
| Experimental example 27 | 60 | 20 | 20 | 15 | 2 |
| Experimental example 28 | 60 | 15 | 25 | 15 | 2 |
| Experimental example 29 | 60 | | 40 | 15 | 2 |
| Experimental example 30 | 60 | 40 | | 20 | 4 |
| Experimental example 31 | 60 | 20 | 20 | 20 | 4 |
| Experimental example 32 | 60 | | 40 | 20 | 4 |
| Experimental example 33 | 60 | 40 | | 20 | 3 |
| Experimental example 34 | 60 | 20 | 20 | 20 | 3 |
| Experimental example 35 | 60 | | 40 | 20 | 3 |
| Experimental example 36 | 60 | 40 | | 20 | 2 |
| Experimental example 37 | 60 | 20 | 20 | 20 | 2 |
| Experimental example 38 | 60 | | 40 | 20 | 2 |

TABLE 4

| Specimen (Plate) | Base material | | | Hydrophilic monomer | Cross-inkable monomer |
| --- | --- | --- | --- | --- | --- |
| | POEA Parts by mass | EA Parts by mass | ETMA Parts by mass | HEMA Parts by mass | BDDA Parts by mass |
| Experimental example 39 | 60 | 20 | 20 | 25 | 4 |
| Experimental example 40 | 60 | | 40 | 25 | 4 |
| Experimental example 41 | 50 | | 50 | 25 | 4 |
| Experimental example 42 | 40 | | 60 | 25 | 4 |
| Experimental example 43 | 30 | | 70 | 25 | 4 |
| Experimental example 44 | 20 | | 80 | 25 | 4 |
| Experimental example 45 | 60 | 20 | 20 | 25 | 3 |
| Experimental example 46 | 60 | | 40 | 25 | 3 |
| Experimental example 47 | 60 | 20 | 20 | 25 | 2 |
| Experimental example 48 | 60 | | 40 | 25 | 2 |
| Experimental example 49 | 60 | | 40 | 35 | 4 |
| Experimental example 50 | 50 | | 50 | 35 | 4 |
| Experimental example 51 | 40 | | 60 | 35 | 4 |
| Experimental example 52 | 60 | | 40 | 40 | 4 |
| Experimental example 53 | 60 | | 40 | 45 | 4 |
| Experimental example 54 | 60 | 40 | | 60 | 4 |
| Experimental example 55 | 60 | 30 | 10 | 20 | 3 |
| Experimental example 56 | 60 | 40 | | 25 | 3 |
| Experimental example 57 | 60 | 30 | 10 | 25 | 3 |
| Experimental example 58 | 60 | 40 | | 25 | 2 |
| Experimental example 59 | 60 | 30 | 10 | 25 | 2 |
| Experimental example 60 | 60 | 10 | 30 | 25 | 2 |

<Measurement of Physical Properties>
(Hydrolysis Treatment)

A specimen was dried at 60° C. in advance, and its pre-treatment mass $W_0$ was measured. 50 mL of distilled water was placed in a 100 mL pressure bottle, and the specimen was immersed therein. The pressure bottle was placed in an incubator at 100° C. and stored therein. Ten plates with a diameter of 6 mm and a thickness of 0.5 mm were used as the specimen. The tare mass $W_{01}$ of the bottle, the mass $W_{02}$ of the bottle after the addition of distilled water, and the mass $W_{03}$ of the bottle after the immersion of the specimen were recorded.

(Dissolution Rate of POEtOH)

The concentration of phenoxyethyl alcohol (POEtOH, hydrolysate of POEA) in the extraction solution and the dissolution rate of POEtOH after 30 days of the hydrolysis treatment were determined using the following procedure. The mass $W_{11}$ of the bottle before collection of the extraction solution was recorded. Then the extraction solution was collected from the bottle, and the mass $W_{12}$ of the bottle after the collection of the extraction solution was recorded. The collected extraction solution, standard solutions, and a blank (distilled water) were analyzed using HPLC. After the analysis, the chromatogram of the distilled water was subtracted from the chromatograms of the collected extraction solution and the standard solutions to perform baseline correction. The area of the peak of POEtOH in each of the corrected chromatograms was calculated. A calibration curve was produced from the POEtOH concentrations and peak areas of the standard solutions. The concentration of POEtOH in the extraction solution was calculated using the area of the peak of POEtOH in the extraction solution and the calibration curve obtained. The dissolution rate of POEtOH per 1 g of the specimen was calculated from formula (1) below using the POEtOH concentration obtained. The volume of the extraction solution was calculated from formula (2). The volume of the extraction solution was calculated based on the following premises. The change in the mass of the specimen during heating at 100° C. is negligibly smaller than the change in the mass of the extraction solution. Since the most part of the extraction solution is water, the computation can be performed using 1 g/mL as the density of the extraction solution without any problem. After the analysis of the extraction solution after 30 days of the hydrolysis treatment, the bottle was again placed in the incubator at 100° C. After a total of 60 days of the hydrolysis treatment, the extraction solution was again collected. The same procedure as that preformed after 30 days of the treatment was repeated. Specifically, the mass $W_{21}$ of the bottle before collection of the extraction solution was recorded. Then the concentration of POEtOH in the extraction solution was quantified by HPLC analysis, and the dissolution rate of POEtOH was calculated from formula (3). The volume of the extraction solution was calculated from formula (4). Similarly, the dissolution rate of POEtOH after a total of 90 days of the hydrolysis treatment was calculated.

The dissolution rate of POEtOH (%)=the concentration of POEtOH in the extraction solution (ppm)×$10^{-6}$×the volume of the extraction solution $V_{1S}$ (mL)/pre-treatment mass $W_0$ (g)×100    Formula (1)

The volume of the extraction solution $V_{1S}$ (mL≈g)= [$W_{02}$ (g)−$W_{01}$ (g)]−[$W_{03}$ (g)−$W_{11}$ (g)]    Formula (2)

The dissolution rate of POEtOH (%)=the concentration of POEtOH in the extraction solution (ppm)×$10^{-6}$×the volume of the extraction solution $V_{2S}$ (mL)/pre-treatment mass $W_0$ (g)×100    Formula (3)

The volume of the extraction solution $V_{2S}$ (mL≈g)=$V_{1S}$ (mL≈g)−[$W_{11}$ (g)−$W_{12}$ (g)]−[$W_{12}$ (g)−$W_{21}$ (g)]    Formula (4)

(Glistening)

In the measurement of glistening, lens-shaped specimens with a diameter of 6 mm and a center thickness of 0.8 mm±0.1 mm or plate specimens with a diameter of 6 mm and a thickness of 0.5 mm were used. The lens-shaped specimens were immersed in water at 35° C. for 17 hours or longer and then immersed in water at 25° C. for 2 hours, and the appearance was observed under a stereoscopic microscope. The plate specimens were immersed in water at 35° C. for 22 hours and then immersed in water at 25° C. for 2 hours, and the appearance was observed under a stereoscopic microscope. In each experimental example, the observation of the appearance was performed on 2 or 3 specimens, and the number of glistening spots (bright spots) formed was examined. The magnification used was about 10× to about 60×. The magnification was appropriately adjusted within the above range so that the glistening was easily observed.

(Water Absorption Percentage)

The mass of each specimen in an equilibrium moisture state and its mass in a dry state were measured, and the water absorption percentage (mass %) of the specimen was calculated. The water absorption percentage was calculated from formula (5) below using the mass $W_w$ of the specimen in the equilibrium moisture state at 25° C. and the mass $W_d$ of the specimen in the dry state. Five plates with a diameter of 6 mm and a thickness of 0.8 mm were used as the specimens.

The water absorption percentage (mass %)=($W_w$−$W_d$)/$W_d$×100    Formula (5)

(Refractive Index)

The refractive index of each specimen was determined using the Mercury e-line in an Abbe refractometer. The measurement was performed on the specimen in a dry state (25° C.) or a moisture state (35° C.). The specimen used was a plate with a diameter of 6 mm and a thickness of 0.8 mm.

(Compressive Load (Plate))

A plate with a diameter of 6 mm and a thickness of 0.5 mm was compressed and buckled (bending buckling) according to the following procedure. Then a load value when the specimen was buckled from 6 mm to 3 mm was measured as a compressive load value. Before the measurement, the specimen was left to stand in an environment at 23° C. and 50% RH to control its state. FIG. 1 is a side view of an indenter 10 and a jig 11 used for the measurement of the compressive load. Each of the indenter 10 and the jig 11 is made of polyoxymethylene (DURACON) and has a cylindrical shape. The indenter 10 and the jig 11 were attached to a creep meter (RE2-33005S manufactured by Yamaden Co., Ltd.). A double-sided adhesive tape (3M Scotch Brand Tape core series 2-0300) was attached to a specimen placement area on the upper surface of the jig 11, and the specimen 12 was placed. A specimen stage (support) with the jig 11 attached thereto was moved up and down to bring the specimen 12 into contact with the indenter 10. The specimen stage was moved up 3.2 mm from the contact position at a compression speed of 0.5 mm/sec to buckle the specimen. A load when the specimen stage was moved up 3 mm was used as the compressive load value.

(Stickiness)

In the measurement of stickiness, a plate with a diameter of 8 mm and a thickness of 0.8 mm was used. A jig for the stickiness measurement was attached to a specimen stage (support) of a creep meter. A part of the jig was detached, and the specimen was fitted into a part of the detached jig. Then the jig integrated with the specimen was attached to the creep meter. The specimen stage was moved to bring the specimen into contact with a metallic probe (radius of curvature: 2.5 mm) such that a force of 0.05 N was applied to the specimen, and the stage was stopped at this position. About 5 seconds after the stage had been stopped, the specimen was separated from the probe at a separation speed of 1 mm/sec, and a load applied to the specimen was measured using the creep meter (RE2-33005S manufactured by Yamaden Co., Ltd.). A value of stickiness was calculated by subtracting the load after the probe had been separated from the specimen (the load after separation) from the maximum load measured. When the stickiness value was 0 N or more and less than 0.16 N, the specimen was rated "A". When the stickiness value was 0.16 N or more and less than 0.30 N, the specimen was rated "B". When the stickiness value was 0.30 N or more, the specimen was rated "C".

(Tensile Test)

Figure 2:
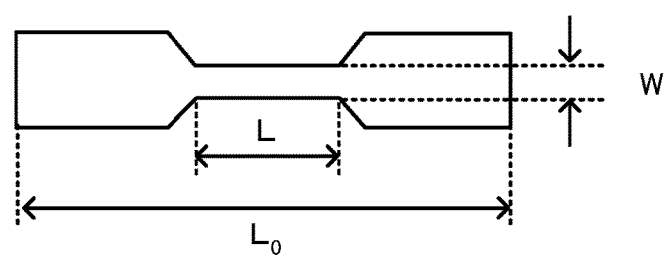
FIG. 2 is an illustration of a specimen used for elongation percentage measurement.

Measurement was performed using a dumbbell-shaped specimen with a total length ($L_0$) of 20 mm, a parallel-portion length (L) of 6 mm, a parallel-portion width (W) of 1.5 mm, and a thickness of 0.8 mm (see FIG. 2). The specimen was immersed in water held at a constant temperature of 25° C., left to stand for 1 minute, and then pulled at a speed of 100 mm/min until break. The strain at the maximum load (=elongation percentage (%)) was determined using software.

(Results and Discussion)

The results for lens-shaped Experimental Examples 1 to 14 are shown in Table 5, and the results for plate-shaped Experimental Examples 15 to 60 are shown in Tables 6 to 9. As can be seen from the results in Tables 6 to 9, the degree of hydrolysis can be reduced by increasing the number of methacrylate structural units, and alkoxymethacrylates are suitable for the methacrylate component. In the compositions of Experimental Examples 1 to 6 in Table 5, the amounts of acrylates (POEA and EA) used as a base material are less than those in the composition described in PTL 1, and POEMA, EHMA, or LMA is added. In the materials of Experimental Examples 1 to 3 to which LMA was added, the stickiness was high. Moreover, the materials were brittle and easily broken, and glistening occurred easily. In the material of Experimental Example 4 to which EHMA was added, glistening occurred easily. In the materials of Experimental Examples 5 and 6 to which POEMA was added, glistening occurred easily, and these materials were hard. However, in the materials of Experimental Examples 7 to 14 to which ETMA, which is an alkoxymethacrylate, was added, the stickiness was low. Moreover, these materials were not brittle.

In the compositions of Experimental Examples 15 to 17 in Table 6, the amounts of acrylates (POEA and EA) used as a base material are less than those in the composition described in PTL 1, and EMA, BMA, or LMA is added. In the material of Experimental Example 15 to which EMA was added, the amount of dissolution of POEtOH was small, and it seemed that the degree of hydrolysis was reduced, but it was obvious that the intraocular lens material was not easily folded. In the material of Experimental Example 16 to which BMA was added, the amount of dissolution of POEtOH was small, and it seemed that the degree of hydrolysis was reduced, but glistening occurred easily. In the material of Experimental Example 17 to which LMA was added, stickiness was high. Moreover, the material was brittle and easily broken, and glistening occurred easily. In the materials of Experimental Examples to which one of MTMA or ETMA, which are alkoxymethacrylates, was added, the amount of dissolution of POEtOH was small, and the degree of hydrolysis was reduced. Moreover, the stickiness was not high. As in 6, the occurrence of glistening was low, and the materials were not brittle.

As can be seen from the results in Tables 5 to 9, a suitable amount of the alkoxymethacrylate added is preferably from 10 parts by mass to 70 parts by mass inclusive and more preferably from 20 parts by mass to 40 parts by mass inclusive based on 100 parts by mass of the base material. The minimum amount of the alkoxymethacrylate is preferably within the above range mainly from the viewpoint of the reduction in the degree of hydrolysis, and the maximum amount of the alkoxymethacrylate is preferably within the above range from the viewpoint of ease of folding and from the viewpoint that no significant burden and difficulty arise during folding.

The amount of the aromatic ring-containing acrylate used as a base material is preferably 30 parts by mass or more based on 100 parts by mass of the base material from the viewpoint that the intraocular lens material in a hydrated state can have a refractive index of 1.50 or more. As the refractive index of the material increases, a thinner lens can be used to obtain a desired refractive power. The thinner the lens, the more easily the folded lens can be inserted into an eye.

The amount of the hydrophilic monomer is preferably 15 parts by mass or more by the outside ratio based on 100 parts by mass of the total amount of the base material from the viewpoint of reducing the occurrence of glistening and is preferably 35 parts by mass or less by the outside ratio in order that no significant burden and difficulty arise during folding in a dry state. When the intraocular lens material in the dry state can be easily bent, the intraocular lens material can be stored, distributed and used in an injector device. The compressive load in Table 8 is a value when the compressive load in Experimental Example 54 is set to 1. The material of Experimental Example 54 was evaluated in PTL 1, and the evaluation indicates that this material can be folded, but a large extra force is necessary. When the compressive load value of a material is equal to or larger than that of the material of Experimental Example 54, a determination is made that a significant burden and difficulty may arise during folding. In Experimental Examples 50 to 53 shown in Table 8, since ETMA was contained, the amount of dissolution of POEtOH was small, and the effect of reducing the degree of hydrolysis was obtained. However, since the amount of ETMA or HEMA was large, the foldability was not good.

The amount of the cross-linkable monomer is preferably 2 parts by mass or more by the outside ratio based on 100 parts by mass of the total amount of the base material from the viewpoint of reducing the occurrence of glistening and from the viewpoint of shape recoverability after insertion into an eye and is preferably 4 parts by mass or less by the outside ratio in order to prevent the elongation of the material to be reduced so that the material does not break easily.

TABLE 5

| Specimen (Lens) | Glistening Number of the spots[1] |
|---|---|
| Experimental example 1 | — |
| Experimental example 2 | — |
| Experimental example 3 | 19 |
| Experimental example 4 | 35 |
| Experimental example 5 | — |
| Experimental example 6 | ∞ |
| Experimental example 7 | 4 |
| Experimental example 8 | — |
| Experimental example 9 | — |
| Experimental example 10 | — |
| Experimental example 11 | — |
| Experimental example 12 | — |
| Experimental example 13 | — |
| Experimental example 14 | — |

[1]Measurement result with lens Average value of number of tests (n = 2 or 3)

TABLE 6

| Speciment (Plate) | Dissolution of POEtOH (100° C., 30 days) ppm | % | Dissolution of POEtOH (100° C., 60 days) ppm | % | Dissolution of POEtOH (100° C., 90 days) ppm | % | Glistening Number of the spots[1] | Stickiness —[2] | Refractive index 25° C. Dry | Refractive index 35° C. Water absorption | Elongation percentage % | Water absorption % |
|---|---|---|---|---|---|---|---|---|---|---|---|---|
| Experimental example 15 | 1 | 0.04 | 4 | 0.11 | 3 | 0.10 | — | — | — | — | — | — |
| Experimental example 16 | 2 | 0.05 | 4 | 0.13 | 5 | 0.15 | 10 | — | — | — | — | — |
| Experimental example 17 | — | — | — | — | — | — | — | — | — | — | 139 | — |
| Experimental example 18 | 3 | 0.08 | 8 | 0.23 | 15 | 0.39 | 2 | — | — | — | — | — |
| Experimental example 19 | 6 | 0.18 | 40 | 1.24 | 192 | 5.57 | 2 | B | 1.523 | 1.517 | — | 1.7 |
| Experimental example 20 | 3 | 0.10 | 15 | 0.43 | 49 | 1.31 | — | — | 1.525 | 1.519 | — | 1.8 |
| Experimental example 21 | 2 | 0.06 | 7 | 0.21 | 15 | 0.41 | 0 | A | 1.527 | 1.522 | — | 1.9 |

[1] Measurement result by a plate with as diameter of 6 mm and a thickness of 0.5 mm. Average value of number of tests (n = 3).
[2] A: 0 N or more and less than 0.16 N, B: 0.16 N or more and less than 0.30 N, C: 0.30 N or more

TABLE 7

| Speciment (Plate) | Dissolution of POEtOH (100° C., 30 days) ppm | % | Dissolution of POEtOH (100° C., 60 days) ppm | % | Dissolution of POEtOH (100° C., 90 days) ppm | % | Glistening Number of the spots[1] | Stickiness —[2] | Refractive index 25° C. Dry | Refractive index 35° C. Water absorption | Elongation percentage % | Water absorption percentage % |
|---|---|---|---|---|---|---|---|---|---|---|---|---|
| Experimental example 22 | 6 | 0.19 | 43 | 1.28 | 205 | 5.80 | — | C | 1.523 | 1.517 | — | 1.6 |
| Experimental example 23 | 3 | 0.11 | 15 | 0.48 | 53 | 1.56 | — | — | 1.525 | 1.519 | — | 1.8 |
| Experimental example 24 | 2 | 0.06 | 5 | 0.16 | 10 | 0.27 | — | A | 1.527 | 1.521 | — | 2.0 |
| Experimental example 25 | 6 | 0.18 | 43 | 1.16 | 209 | 5.29 | — | C | 1.523 | 1.518 | — | 1.6 |
| Experimental example 26 | 5 | 0.13 | 25 | 0.67 | 111 | 2.76 | — | — | — | — | — | — |
| Experimental example 27 | 3 | 0.09 | 16 | 0.40 | 51 | 1.24 | — | — | 1.525 | 1.519 | — | 1.8 |
| Experimental example 28 | 3 | 0.09 | 12 | 0.32 | 33 | 0.86 | — | — | — | — | — | — |
| Experimental example 29 | 2 | 0.05 | 6 | 0.16 | 11 | 0.28 | — | — | 1.527 | 1.521 | 345 | 2.1 |
| Experimental example 30 | 5 | 0.16 | 36 | 1.06 | 162 | 4.48 | — | B | 1.522 | 1.516 | — | 2.1 |
| Experimental example 31 | 3 | 0.10 | 15 | 0.41 | 44 | 1.17 | — | B | 1.524 | 1.518 | — | 2.4 |
| Experimental example 32 | 2 | 0.06 | 6 | 0.17 | 10 | 0.28 | — | A | 1.527 | 1.521 | — | 2.4 |
| Experimental example 33 | 5 | 0.15 | 33 | 0.97 | 150 | 4.09 | — | B | 1.522 | 1.516 | — | 2.3 |
| Experimental example 34 | 3 | 0.09 | 12 | 0.37 | 38 | 1.06 | 0 | B | 1.524 | 1.518 | — | 2.2 |
| Experimental example 35 | 2 | 0.06 | 6 | 0.18 | 10 | 0.29 | — | A | 1.527 | 1.520 | — | 2.7 |
| Experimental example 36 | 6 | 0.17 | 38 | 1.03 | 176 | 4.47 | — | C | 1.522 | 1.516 | — | 2.2 |
| Experimental example 37 | 3 | 0.08 | 13 | 0.33 | 41 | 0.97 | 1 | B | 1.524 | 1.518 | — | 2.5 |
| Experimental example 38 | 2 | 0.06 | 6 | 0.17 | 12 | 0.30 | — | A | 1.527 | 1.520 | — | 2.8 |

1) Measurement result by a plate with as diameter of 6 mm and a thickness of 0.5 mm. Average value of number of tests (n = 3).
2) A: 0 N or more and less than 0.16 N, B: 0.16 N or more and less than 0.30 N, C: 0.30 N or more

TABLE 8

| Speciment (Plate) | Dissolution of POEtOH (100° C., 30 days) ppm | % | Dissolution of POEtOH (100° C., 60 days) ppm | % | Dissolution of POEtOH (100° C., 90 days) ppm | % | Glistening Number of the spots[1] | Stickiness —[2] | Refractive index 25° C. Dry | 35° C. Water absorption | Compressive load —[3] | Water absorption percentage % |
|---|---|---|---|---|---|---|---|---|---|---|---|---|
| Experimental example 39 | 3 | 0.09 | 13 | 0.36 | 37 | 0.95 | — | A | 1.524 | 1.517 | — | 3.1 |
| Experimental example 40 | 2 | 0.06 | 6 | 0.18 | 10 | 0.28 | — | A | 1.526 | 1.520 | — | 3.3 |
| Experimental example 41 | 2 | 0.06 | 5 | 0.16 | 7 | 0.19 | — | — | 1.520 | 1.512 | — | — |
| Experimental example 42 | 2 | 0.05 | 4 | 0.13 | 3 | 0.10 | — | — | 1.514 | 1.507 | — | — |
| Experimental example 43 | 2 | 0.06 | 5 | 0.13 | 4 | 0.10 | — | — | 1.509 | 1.500 | 0.7 | — |
| Experimental example 44 | 1 | 0.04 | 3 | 0.09 | 1 | 0.02 | — | — | 1.503 | 1.495 | — | — |
| Experimental example 45 | 2 | 0.07 | 10 | 0.29 | 29 | 0.79 | 1 | A | 1.524 | 1.517 | — | 3.0 |
| Experimental example 46 | 2 | 0.05 | 5 | 0.16 | 8 | 0.23 | — | A | 1.526 | 1.520 | — | 3.1 |
| Experimental example 47 | 3 | 0.09 | 13 | 0.34 | 36 | 0.88 | — | B | 1.524 | 1.517 | — | 3.0 |
| Experimental example 48 | 2 | 0.06 | 6 | 0.17 | 11 | 0.29 | — | A | 1.526 | 1.519 | — | 3.2 |
| Experimental example 49 | 2 | 0.06 | 6 | 0.19 | 10 | 0.28 | — | — | — | — | 0.8 | — |
| Experimental example 50 | 2 | 0.06 | 5 | 0.15 | 6 | 0.17 | — | — | 1.520 | 1.510 | 1.1 | — |
| Experimental example 51 | 2 | 0.05 | 4 | 0.12 | 4 | 0.10 | — | — | 1.514 | 1.504 | 1.3 | — |
| Experimental example 52 | 2 | 0.07 | 7 | 0.19 | 12 | 0.29 | — | — | — | — | 1.8 | — |
| Experimental example 53 | 2 | 0.06 | 9 | 0.18 | 8 | 0.23 | — | — | — | — | 1.6 | — |
| Experimental example 54 | — | — | — | — | — | — | — | — | — | — | 1.0 | — |

[1]Measurement result by a plate with as diameter of 6 mm and a thickness of 0.5 mm. Average value of number of tests (n = 3).
[2]A: 0 N or more and less than 0.16 N, B: 0.16 N or more and less than 0.30 N, C: 0.30 N or more
[3]Each value of experimental examples is standardized by determining the compressive load of experimental example 54 as "1".

TABLE 9

| Specimen (Plate) | Dissolution of POEtOH (100° C., 30 days) ppm | % | Dissolution of POEtOH (100° C., 60 days) ppm | % | Dissolution of POEtOH (100° C., 90 days) ppm | % |
|---|---|---|---|---|---|---|
| Experimental example 55 | 5 | 0.14 | 24 | 0.66 | 91 | 2.33 |
| Experimental example 56 | 5 | 0.15 | 31 | 0.83 | 134 | 3.33 |
| Experimental example 57 | 5 | 0.13 | 23 | 0.61 | 79 | 1.92 |
| Experimental example 58 | 4 | 0.14 | 28 | 0.82 | 119 | 3.31 |
| Experimental example 59 | 5 | 0.13 | 23 | 0.60 | 79 | 1.96 |
| Experimental example 60 | 3 | 0.09 | 11 | 0.30 | 25 | 0.63 |

The present application claims priority from Japanese Patent Application No. 2016-148426 filed on Jul. 28, 2016, the entire contents of which are incorporated herein by reference.

INDUSTRIAL APPLICABILITY

The invention disclosed in the present description can be used for intraocular lens applications.

REFERENCE SIGNS LIST

10 indenter, 11 jig, 12 specimen.

The invention claimed is:

1. An intraocular lens material comprising:
an aromatic ring-containing acrylate structural unit;
an alkoxyalkyl methacrylate structural unit including an alkoxyalkyl group having 4 or less carbon atoms;
an alkyl acrylate structural unit including an alkyl group having 1 to 20 carbon atoms,
a hydrophilic structural unit based on a hydrophilic monomer;
a cross-linking structural unit based on a cross-linkable monomer,
wherein the aromatic ring-containing acrylate structural unit is phenoxyethyl acrylate structural unit,
the alkoxyalkyl methacrylate structural unit is an ethoxyethyl methacrylate structural unit,
the alkyl acrylate structural unit is an ethyl acrylate structural unit, and
a base material consists of the aromatic ring-containing acrylate structural unit, the alkoxyalkyl methacrylate structural unit and the alkyl acrylate structural unit, and the base material include one kind of the aromatic ring-containing monomer.

2. The intraocular lens material according to claim 1, wherein the alkoxyalkyl methacrylate structural unit is included in an amount within the range of from 10 parts by mass to 70 parts by mass inclusive based on 100 parts by mass of the total amount of the base material.

3. The intraocular lens material according to claim 1, wherein the alkoxyalkyl methacrylate structural unit is included in an amount within the range of from 10 parts by mass to 40 parts by mass inclusive based on 100 parts by mass of the total amount of the base material.

4. The intraocular lens material according to claim 1, wherein the hydrophilic structural unit is included in an amount within the range of from 15 parts by mass to 35 parts by mass inclusive by the outside ratio based on 100 parts by mass of the total amount of the base material.

5. The intraocular lens material according to claim 1, wherein the cross-linking structural unit is included in an amount within the range of from 2 parts by mass to 4 parts by mass inclusive by the outside ratio based on 100 parts by mass of the total amount of the base material.

6. The intraocular lens material according to claim 1, wherein the alkyl acrylate structural unit is included in an amount within the range of from 10 parts by mass to 35 parts by mass inclusive based on 100 parts by mass of the total amount of the base material.

7. The intraocular lens material according to claim 1, wherein the aromatic ring-containing acrylate structural unit is included in an amount within the range of from 15 parts by mass to 80 parts by mass inclusive based on 100 parts by mass of the total amount of the base material.

8. The intraocular lens material according to claim 1, wherein the hydrophilic structural unit is a hydroxyethyl methacrylate structural unit.

9. The intraocular lens material according to claim 1, wherein the cross-linking structural unit is a butanediol diacrylate structural unit.

10. The intraocular lens material according to claim 1, wherein the aromatic ring-containing acrylate structural unit is included in an amount within the range of from 30 parts by mass to 80 parts by mass inclusive based on 100 parts by mass of the total amount of the base material,
   the alkoxyalkyl methacrylate structural unit is included in an amount within the range of from 10 parts by mass to 40 parts by mass inclusive based on 100 parts by mass of the total amount of the base material,
   the alkyl acrylate structural unit is included in an amount within the range of from 10 parts by mass to 35 parts by mass inclusive based on 100 parts by mass of the total amount of the base material.

* * * * *